(12) United States Patent
Cecchetti

(10) Patent No.: US 6,358,242 B1
(45) Date of Patent: Mar. 19, 2002

(54) POST LASER TREATMENT FOR PERMANENT HAIR REMOVAL

(75) Inventor: Walter Cecchetti, Saonara (IT)

(73) Assignee: CeramOptec Industries, Inc., East Longmeadow, MA (US)

( * ) Notice: Subject to any disclaimer, the term of this patent is extended or adjusted under 35 U.S.C. 154(b) by 0 days.

(21) Appl. No.: 09/439,255

(22) Filed: Nov. 12, 1999

(51) Int. Cl.$^7$ ................................................ A61B 18/18
(52) U.S. Cl. ........................ 606/9; 606/131; 606/133; 128/898; 607/88; 607/89
(58) Field of Search ............................... 606/3, 9, 127, 606/128, 131, 133, 134; 607/88, 89; 128/898

(56) References Cited

U.S. PATENT DOCUMENTS

| | | | | |
|---|---|---|---|---|
| 5,425,728 A | * | 6/1995 | Tankovich et al. | 606/9 |
| 5,489,279 A | | 2/1996 | Meserol | |
| 5,752,948 A | * | 5/1998 | Tankovich et al. | 606/9 |
| 5,752,949 A | | 5/1998 | Tankovich et al. | |
| 5,846,252 A | | 12/1998 | Mehl, Sr. | |
| 5,853,407 A | | 12/1998 | Miller | |
| 5,989,267 A | * | 11/1999 | Anderson | 606/133 |
| 6,050,990 A | * | 4/2000 | Tankovich et al. | 606/9 |
| 6,143,287 A | * | 11/2000 | Ben-Hur et al. | 424/73 |
| 6,183,773 B1 | * | 2/2001 | Anderson | 424/450 |
| 6,219,575 B1 | * | 4/2001 | Nemati | 604/20 |
| 6,267,771 B1 | * | 7/2001 | Tankovich et al. | 606/131 |

* cited by examiner

Primary Examiner—Linda C. M. Dvorak
Assistant Examiner—Ahmed Farah
(74) Attorney, Agent, or Firm—Bolesh J. Skutnik; BJ Associates

(57) ABSTRACT

A method too permanently remove unwanted hair using a diode or other laser source in a post-treatment mode is disclosed. The method is not limited by skin pigmentation, causes no pain, and minimizes damage to surrounding tissue. The hair in the treatment area is first removed using conventional stripping techniques leaving the hair follicles substantially empty. While the follicles are still open, a special photosensitizing lotion is rubbed into the skin and then penetrates in the depth of the follicle. A solvent is then used to clean the surface of the skin from excess photosensitizer, while the photosensitizer remains in the follicles. In this way, the follicular ducts are selectively sensitized. An area containing the follicles is then irradiated by a diode laser in the near IR range and the follicles are thereby killed. There is no waiting time necessary in between different steps of treatment and generally only one application of laser radiation is required. The photosensitizer of the present invention may operate through photochemical or photothermal action.

10 Claims, 6 Drawing Sheets

Radiation effects on biological tissue.

FIGURE 1  Radiation effects on biological tissue.

POST LASER TREATMENT FOR PERMANENT HAIR REMOVAL

BACKGROUND OF INVENTION

1. Field of the Invention

This invention relates to a photothermal and/or a photochemical process induced by laser radiation to destroy hair follicles and to prevent hair growth after traditional hair stripping.

2. Invention Disclosure Statement

Techniques for removal of unwanted hair have traditionally been electrolysis and chemical or wax depilatories. Such techniques, when used by themselves, must be repeated several times to ensure a semi-permanent effect. Thus, these techniques used alone consume excessive time and expose the patient to repeated painful treatments.

As an alternative to these conventional treatments, lasers have also been used to remove unwanted hair with significant benefits. Many problems still exist, however, with state of the art hair removal systems. The most significant problems are low permanent hair removal percentage and complexity of operation.

U.S. Pat. No. 5,425,728, "Hair Removal Device and Method", Tankovich, describes a system of permanent laser hair removal. After shaving the hairs in a treatment area to a height of 1 mm above the skin, hair on a section of skin is contaminated with a carbon oil substance having high absorption of a frequency band of light. The skin is illuminated with light at this frequency band by a Nd:YAG laser at sufficient intensity and duration to kill the follicles or the skin tissue feeding the hair. This is carried out by either photothermal or photochemical reactions. After the laser treatments, a 30% hair reduction resulted. The problem with this invention is that it is difficult for the carbon oil absorber to penetrate to the depth of the hair follicle while the hair is still in place. Another problem is low percentage hair reduction.

The problem of penetration was addressed in a later patent by Tankovich, Zhao, and Fairchild. U.S. Pat. No. 5,752,949 entitled "Hair Removal Method" which describes a method whereby photosensitizers are activated in two distinct phases. In a "mechanical" phase, the skin section is illuminated (e.g. by a laser) with at least one short pulse of light sufficient to cause tiny explosions in the contaminant forcing portions of the contaminant more deeply into the hair ducts. During a "thermal" phase the skin section is then illuminated so as to heat the contaminant substantially without further explosion or vaporization of the contaminant. This is a complicated means of achieving hair duct penetration.

Yet another patent by Tankovich, et al, U.S. Pat. No. 5,752,948 also entitled "Hair Removal Method" further addressed the problem of hair duct penetration. In one embodiment of this patent, the hairs in the section of skin being treated are pulled out prior to application of the contaminant so as to provide more space for the contaminant in the hair duct. In another preferred embodiment, a portion of the hairs below the skin surface is removed with a depilatory. Admitting that effective permanent hair removal largely depends upon good penetration of the photosensitizer into the hair duct, this patent attempts to offer solutions to this problem. However, this invention does not allow for chemically acting photosensitizers to be used. It also makes use of carbon particulate matter, not a smooth lotion for application of photosensitizers. It is more difficult for the carbon particles to penetrate to the depth of the follicle because of their particle size. Lastly, in a particularly preferred embodiment of this invention, the inventors recommend leaving the photosensitizing lotion on the surface of the skin. This practice may expose the skin surface to excessive radiation and be damaging to the skin.

The process described in U.S. Pat. No. 5,752,948 is also overly invasive. It is a photomechanical process that utilizes laser energy to raise treatment temperatures to such a degree that explosive ablation and optical breakdown occur. Such a process is unnecessary for the given result. In contrast, the present invention utilizes a continuous wave laser. The laser energy produced by the present invention does not need to raise the temperature of the treatment site higher than 70° C. Therefore, the present invention allows us to work at more benign, less harmful temperatures.

U.S. Pat. No. 5,853,407 entitled "Method and Apparatus for Hair Removal", by Miller, has another approach to permanent laser hair removal. This invention uses pulsed coherent light of selected wavelength and peak power level and post duration, and repeating the coherent laser irradiation on one or more subsequent occasions with selected light parameters. The specific target for laser radiation described in this disclosure is the melanin within the hair shaft and within the melanocytes lining the follicular duct. Targeting melanin with radiation, however, has the undesirable side effect of changing skin pigmentation. This invention is overly complicated and time-consuming because it requires two or more radiative treatments to be performed with a healing time of 1–3 months between each treatment.

Yet another means of permanent laser hair removal is found in U.S. Pat. No. 5,846,252 entitled "Method of Removing Hair from the Body and Inhibiting Future Growth", by Mehl. This patent describes a method for the removal of hair through the use of electromagnetic (e.g., AC, DC, blend, and laser) energy by treatment of the hair prior to the application of such electromagnetic energy to reduce the electromagnetic energy resistance of the hair. This electrochemical removal process does not provide for hairs to be removed prior to irradiation since in this invention the hair itself is used to conduct electricity into the follicle. This method is very time-consuming because it requires individual removal of hair.

In U.S. Pat. No. 5,489,279, by Meserol and assigned to DUSA Pharmaceuticals employs light-activated topical photopharmaceutical 5-ALA (a drug used to treat cancer in PhotoDynamic Therapy, available from the Sigma Chemical Company, St. Louis, Mo.), to photochemically oxidize and thus destroy proliferous cellular components of the follicle.

Thus, state of the art laser hair removal methods offer improvements over more conventional methods. They can be relatively quick and painless operations. They still have drawbacks, however. The main drawback is that all of the above techniques have a low permanent hair reduction percentage. Another common drawback to many of these techniques is that the hair and the follicle must be destroyed by the radiation. Thus, more body tissue must be destroyed by radiation. Furthermore, many state of the art hair removal systems involve radiation of melanin which causes depigmentation, an undesirable side effect. Additionally, state of the art laser hair removal techniques propose the use of overly complex and expensive lasers.

Diode lasers possess many advantages when compared to other types of lasers, including Nd:YAG and ruby lasers, as mentioned above. They are efficient, inexpensive, compact and easy to operate and maintain.

Thus, a hair removal system that provides the advantages of a low cost diode laser with improved permanence of hair removal, low residual melanin absorption to avoid depigmentation at the treatment site, and a short treatment period is needed.

It is therefore the aim of the present invention to provide a laser hair removal method which addresses these shortcomings.

SUMMARY AND OBJECTIVES

It is an object of the present invention to provide a method for permanent hair removal using a diode laser system to avoid the complexities of state of the art laser hair removal systems.

Another object of the present invention is to provide a method for permanent hair removal whereby hair is first removed by conventional stripping means before laser radiation is applied, to prevent excessive tissue damage.

Yet another object of the present invention is to provide a method for permanent hair removal whereby a photosensitizer is used to absorb laser radiation and aid in the destruction of hair follicles.

Still another object of the present invention is to provide a means for permanent laser hair removal using photochemical and/or photothermal processes.

A further object of the present invention is to provide a means for permanent laser hair removal which does not require long treatment periods or waiting periods between treatments.

Another object of the present invention is to provide a means for permanent laser hair removal with minimal melanin absorption ensuring that any detrimental pigmentation effects are minimized or reduced, contrary to treatments using prior art methods.

Briefly stated, the present invention provides a means to permanently remove unwanted hair using a diode laser or other laser source in a post-treatment mode. The hair in the treatment area is first removed using conventional stripping techniques leaving the hair follicles substantially empty. While the follicles are open, a special photosensitizing lotion is rubbed into the skin and until it penetrates into the depth of the follicle. A solvent is used to clean the surface of the skin from excess photosensitizer, leaving the photosensitizer in the follicles. In this way, the follicular ducts are selectively sensitized. The follicles are then irradiated by a diode laser in the near IR range and the follicles are thereby killed. There is no waiting time necessary in between different steps of treatment and only one application of laser radiation is generally required. Also, the present invention can operate through the activation of chemically acting or thermally acting photosensitizers.

The above, and other objects, features and advantages of the present invention will become apparent from the following description read in conjunction with the accompanying drawings, in which like reference numbers in different drawings denote like items.

DETAILED DESCRIPTION OF PREFERRED EMBODIMENTS

Figure 1:
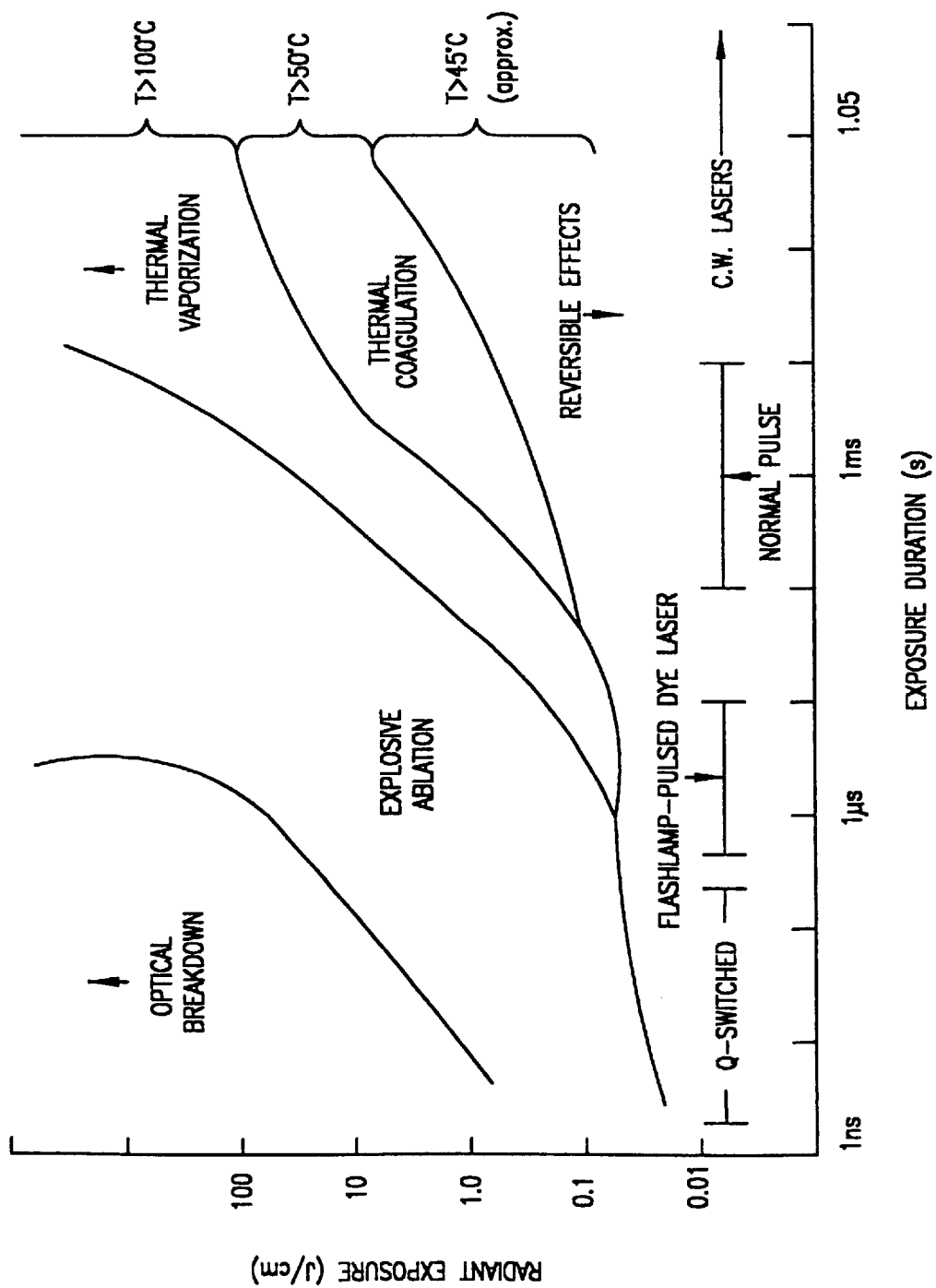
FIG. 1 is a chart illustrating the effects of radiation on biological tissues.
Figure 2:
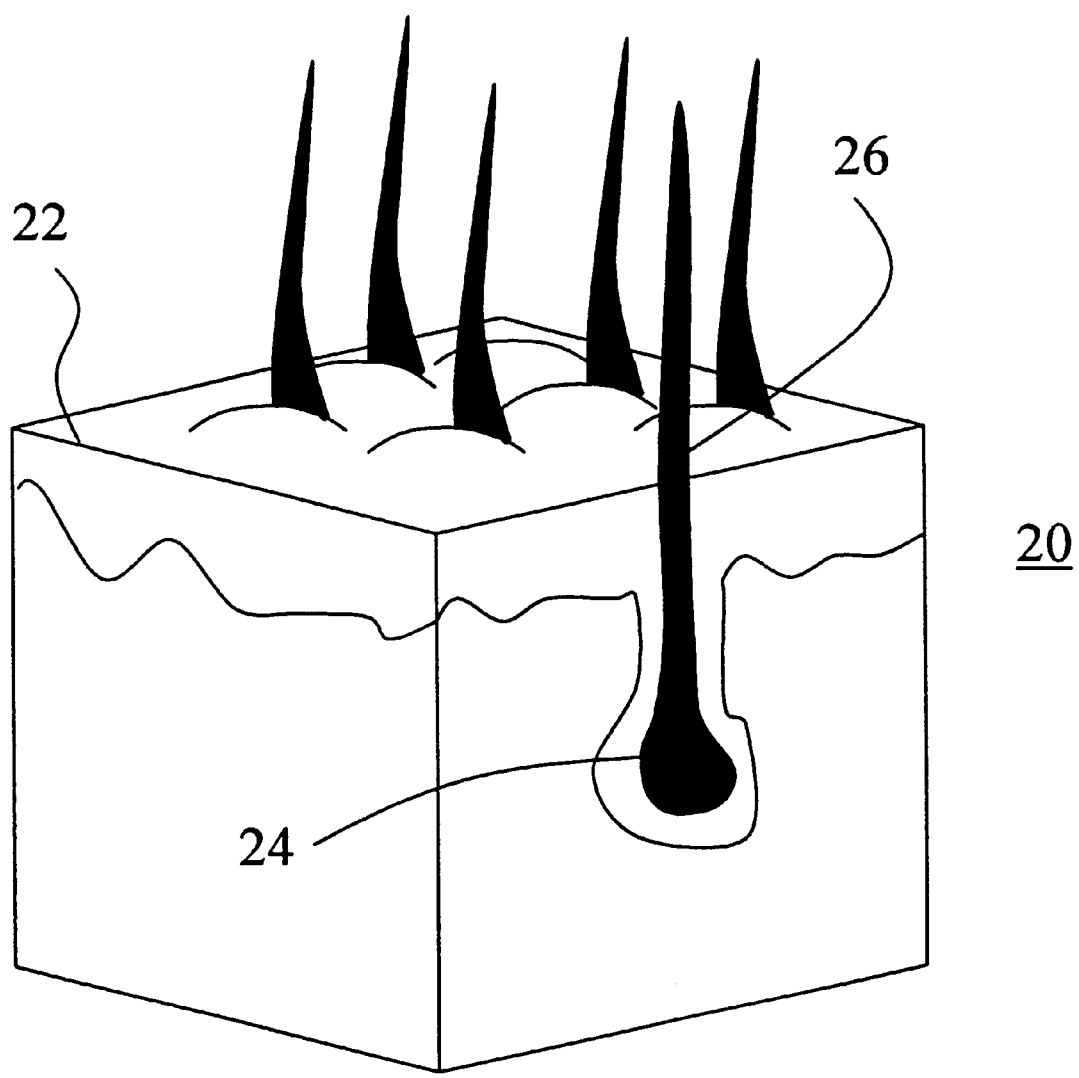
FIG. 2 Shows a hair follicle duct containing hair.
Figure 3:
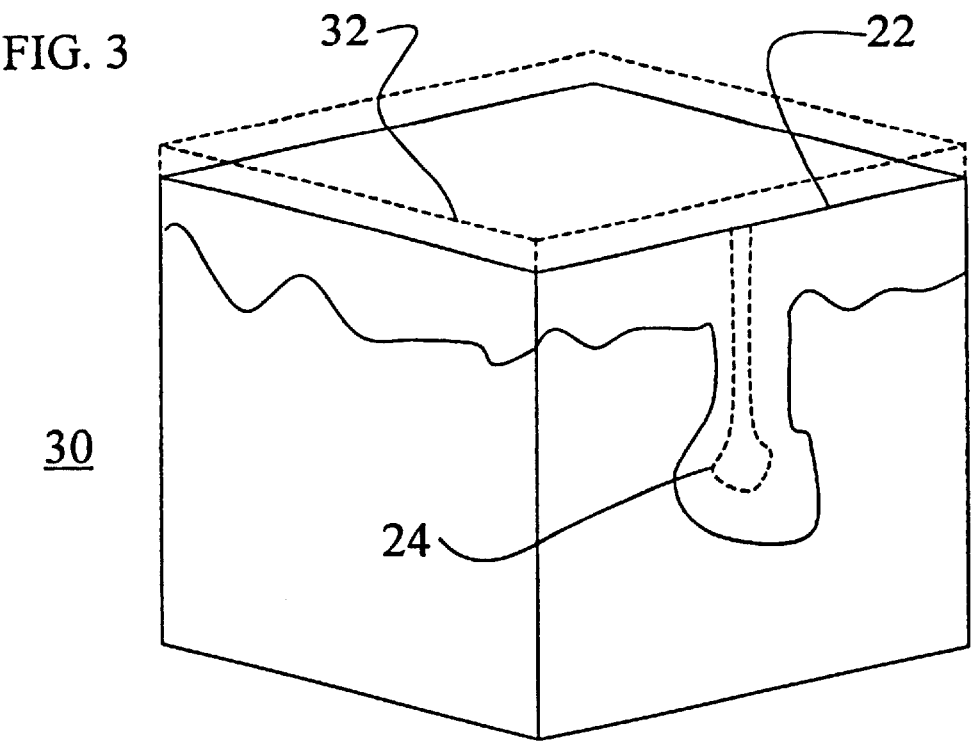
FIG. 3 Shows an empty hair follicle after conventional stripping, the photosenstizer lotion/cream is applied and absorbed.
Figure 4:
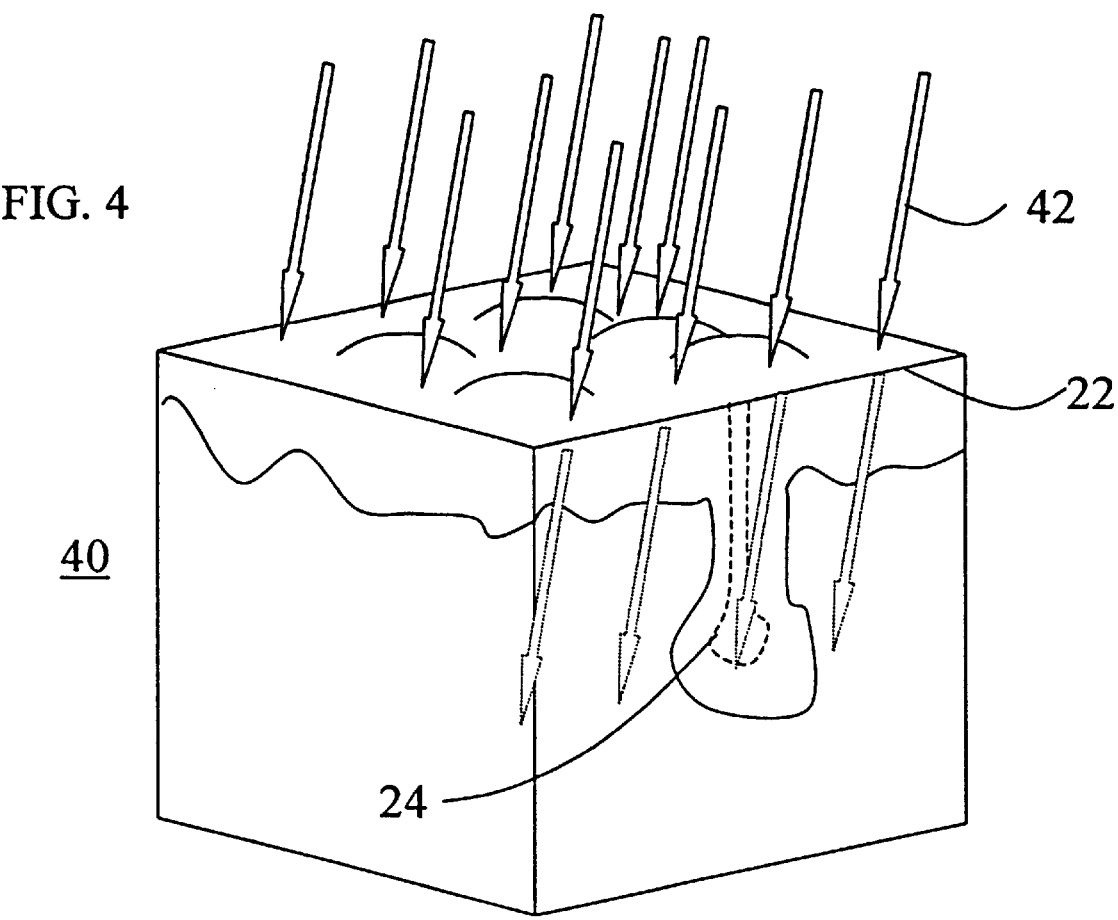
FIG. 4 Shows the skin after the photosensitizer is wiped away and the photosensitizer remains only in the empty hair follicle. The follicles are then irradiated by a laser.
Figure 5:
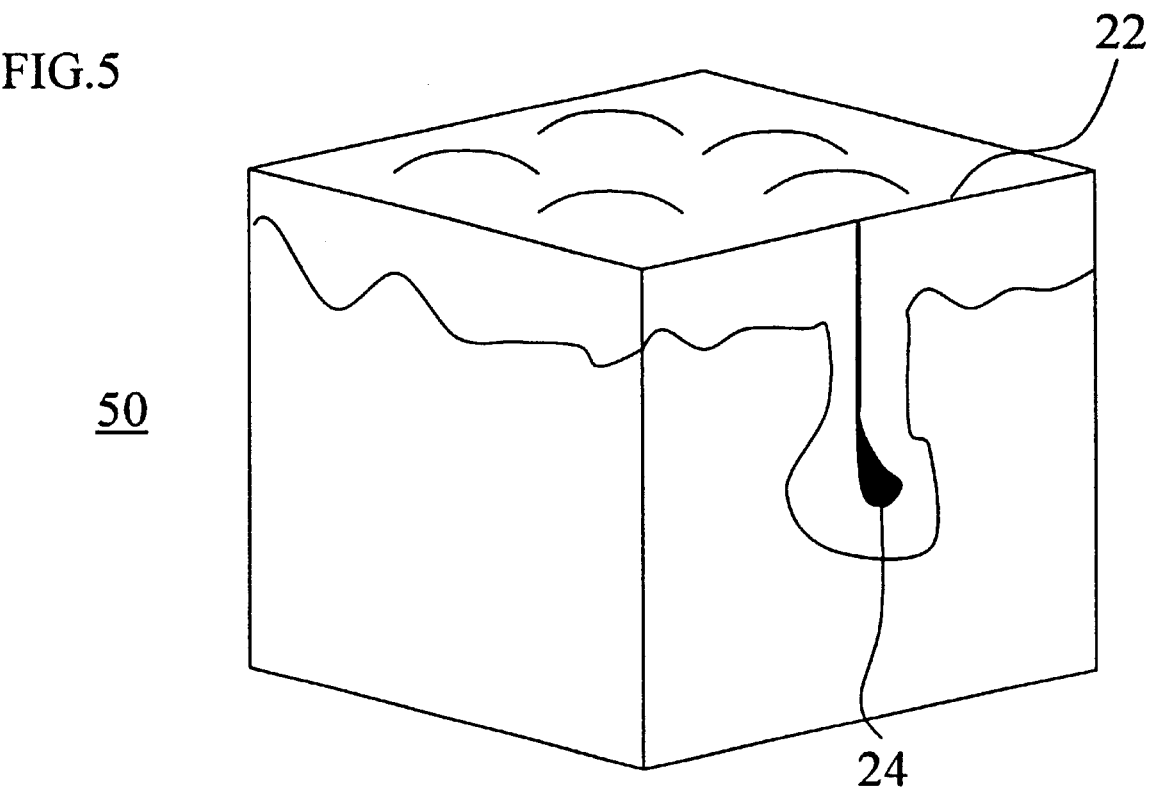
FIG. 5 Shows the shrinking of the follicle after photosensitization treatment.

The present invention describes both photochemical and photothermal processes to shrink hair follicles. Two processes are described that are less invasive, less harmful and more effective than traditional photomechanical ablation. Provided is a method for permanent hair removal using laser post-treatment. FIG. 1 illustrates the effect of radiation on biological tissues during photothermal treatment with the present invention. Continuous wave (C.W.) laser energy (at treatment durations of 1 second) is used. Tissue at the treatment site reaches temperatures in the range of 50–70° C. Within that temperature range and treatment duration, thermal coagulation results (which is highly desirable). Contrast, prior art treatment methods operating with Q-switched laser energy provided at short durations (less than 1 $\mu$s), and raising tissue temperature to above 70° C. These treatment methods cause explosive ablation and even optical breakdown (both invasive and undesirable side effects). In FIG. 2, treatment area 20 has hair 26, located in follicle 24. In a preferred embodiment, hair 26 as well as tens or hundreds of other-like hairs in the same area are stripped out of the follicles using conventional stripping means such as wax or chemical epilation, leaving the follicles open. With hair follicle 24 open, photosensitizing lotion 32 in FIG. 3 is massaged into the treatment area and penetrates into the depth of follicle 24. With excess photosensitizing lotion 32 covering skin surface 22, a solvent is applied to remove the lotion from skin surface 22, leaving lotion only in the hair follicle. The follicles are thereby selectively pre-sensitized to the radiation. An area of skin containing the sensitized follicles is then irradiated with a diode laser, at a wavelength that is selected according to what type of photosensitizer is used. Irradiation 42 in FIG. 4 is applied to the entire treatment area. As radiation is applied to the treatment area, the follicles 24 are selectively damaged and collagen shrinkage in the follicle 24 occurs as in treated area 50 of FIG. 5. Through these steps, hair once removed is prevented from regrowing in the treated follicle(s).

Radiation from the diode laser may be separately administered at at least two different wavelengths, e.g. 670 nm and 780 nm. These wavelengths are selected because they offer optimal dermal penetration. They also afford protection for overlying tissue structures because these wavelengths are not absorbed by these structures. Also at these wavelengths, there is low residual melanin absorption, and therefore the undesirable depigmentation effect is diminished.

Additional variants arise from the fact that photosensitizer lotions of two different types may be used, thermal acting photosensitizers and chemical acting photosensitizers. Thermal acting photosensitizers sterilize follicles by raising the temperature of the follicles to above 50° C., generally about 65° C. This effects shrinkage of collagen cells in the follicle, but does not cause any necrosis or aesthetic damage to the skin surface. Chemically acting photosensitizers destroy follicles in about two days through a process of necrosis by singlet oxygen.

For each activator wavelength, there is generally a thermally acting photosensitizer and a chemically acting photosensitizer that may be used. At 670 nm, Methylene Blue 0.05% may be used as a thermally acting photosensitizer and (Zn(II) pc) zincphthalocyanine ($10^{-7}$M solution), or Tin Ethyl Etiopurpurin (SnET$_2$) ($10^{-6}$M solution) may be used as a chemically acting photosensitizer. At 780 nm, different compounds are used. For example, ICG (Sterile Indocyanine Green) 0.0125% may be used as a thermally acting photosensitizer. Butoxy silicon naphthalocyanine (BOSiNc) ($10^{-5}$M solution) can be used as a chemically acting photosensitizer. These photosensitizers can be used individually or in combination to maximize their effectiveness.

EXAMPLE

To treat an area of skin for permanent hair removal, an activator wavelength of 670 nm is selected. Methylene Blue 0.05% solution is then selected as a thermally acting photosensitizer. The first step taken, before application of the photosensitizer and irradiation, is the stripping of hair in the area using conventional stripping methods. After stripping, while the follicle ducts are open, the photosensitizer lotion is massaged into the skin in the treatment area and thereby achieves complete penetration of the photosensitizer into the follicles. Several minutes later, excess photosensitizer lotion is removed from the skin surface using a solvent, leaving photosensitizer only in the follicles. A handpiece containing a 2W diode laser is used to directly irradiate the skin. This irradiation is enough to activate the photosensitizer in a short period of time. Selective damage is thereby induced only inside the follicles, and not on the skin surface. For 0.05% Methylene blue solution, radiation is applied at 670 nm by a diode laser depositing 2W/cm$^2$ for 25 seconds.

For 0.01% solution of ICG (Sterile Indocyanine Green), radiation is deposited at 780 $\mu$m by a diode laser at 800 mW/cm$^2$ for 25 seconds. A good photothermal effect is achieved, resulting in shrinkage of the collagen cells and follicle sterilization without aesthetic damage to the skin surface either during or following treatment.

For Zn(II)Pc, radiation is applied at 670 nm by a diode laser at 200 mW/cm$^2$ for 100 seconds. A good photochemical effect is achieved, resulting in a necrosis of the follicle with no aesthetic damage to the skin surface during or after treatments. By this means, permanent hair removal is achieved. The dose rate necessary to obtain the photothermal or photochemical effects depends on the photosensitizer concentration, the power density of the laser, the desired time of irradiation, and the area over which radiation will be applied.

The entire process may be carried out in a period of minutes, depending upon the size of the treatment area, because only one laser treatment is required. This is much easier and more convenient than other laser hair removal systems which require lengthy periods of waiting and/or healing in between subsequent radiation treatments.

Figure 6:
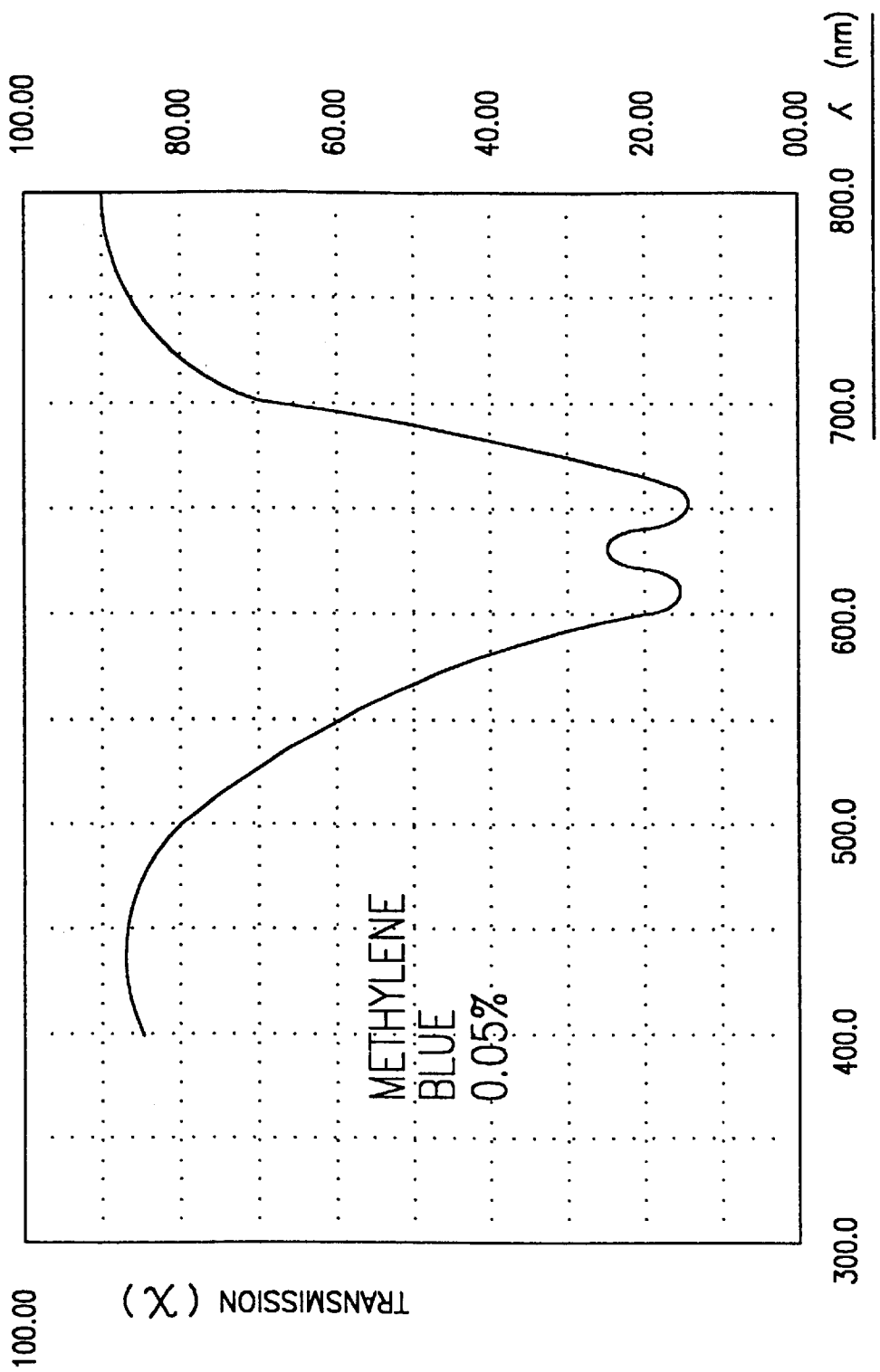
FIG. 6 Shows the spectra for methylene blue 0.05% solution (a thermally acting photosensitizer).

FIG. 6 shows the transmission spectrum for the thermally acting photosensitizer Methylene Blue (0.05%). From the figure it can be seen that Methylene Blue (0.05%) has the lowest transmission value around 670 nm, which corresponds to the wavelength administered during treatment. In other words, Methylene Blue (0.05%) is most absorptive of radiation administered with a wavelength of 670 nm.

Figure 7:
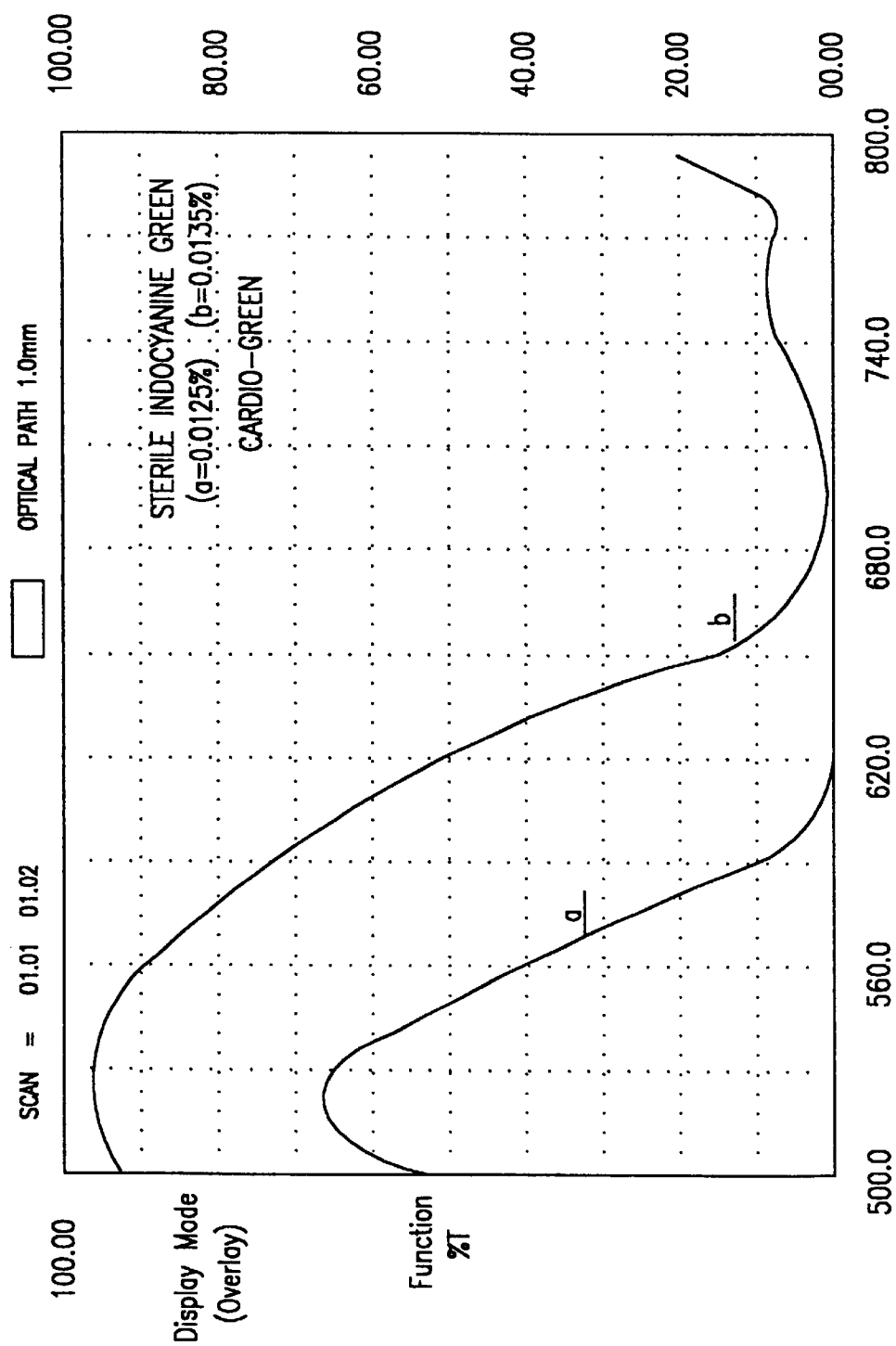
FIG. 7 Shows the spectra for ICG (Sterile Indocyanine Green) 0.125% solution (also a thermally acting photosensitizer).

FIG. 7 shows the transmission spectrum for the thermally acting photosensitizer Sterile Indocyanine Green (ICG). Most importantly, it shows that ICG at a concentration near 0.0135% has the greatest absorptivity (the lowest transmission) at wavelengths between 700–800 nm. Therefore, treatment administered with ICG (0.0135%) as the photosensitizer, would employ radiation at a wavelength within that range.

Having described preferred embodiments of the invention with reference to the accompanying drawings, it is to be understood that the invention is not limited to these precise embodiments, and that various changes and modifications may be effected therein by one skilled in the art without departing from the scope or spirit of the invention as defined in the appended claims.

What is claimed is:

1. A method of permanent hair removal by laser post-treatments after conventional hair stripping, which is not limited by skin pigmentation, causes no pain, minimizes damage to surrounding tissue, and which utilizes a photosensitizer; comprising the steps of:
   a) selecting a photosensitizer that will activate at a wavelength that will not be limited by skin pigmentation and that has low residual melanin absorption to avoid depigmentation;
   b) applying said photosensitizer onto an area of skin treated by a conventional hair stripping process, so as to impregnate hair follicles within hair ducts within said area of skin;
   c) applying a solvent wipe to remove excess photosensitizer from said area of skin without significantly removing said photosensitizer from said hair follicles;
   d) selecting a laser delivery system for treatment based on said photosensitizer's activation wavelength;
   e) irradiating said area of skin with said laser delivery system; and
   f) whereby said photosensitizer in said impregnated hair follicles is activated and said impregnated hair follicles are destroyed with minimal damage to skin or other tissue surrounding said hair follicles.

2. A method of permanent hair removal according to claim 1, wherein said photosensitizer contains materials which act by photochemically destroying said hair follicles.

3. A method of permanent hair removal according to claim 1, wherein said photosensitizer photothermally destroys said hair follicles without raising the temperature of a treatment area above about 70° C.

4. A method of permanent hair removal according to claim 1 wherein said photosensitizer contains materials, which act both photochemically, and photothermally to destroy said hair follicles.

5. A method of permanent hair removal according to claim 1, wherein said photosensitizer is applied in a form selected from the group consisting of lotions, creams, and gaseous preparations.

6. A method of permanent hair removal according to claim 1, wherein said irradiating step is performed with said laser delivery system in contact with said treated area of skin.

7. A method of permanent hair removal according to claim 1, wherein said irradiating step is performed with said laser delivery system not in contact with said treated area of skin.

8. A method of permanent hair removal according to claim 1, comprising a further step in conjunction with said irradiating step of:
   e$_1$) regulating temperature of said area of skin under treatment.

9. A method of permanent hair removal according to claim 8, wherein said regulating temperature includes providing cooling to said area of skin.

10. A method of permanent hair removal according to claim 8, wherein said regulating temperature includes providing heated fluid to said area of skin.

* * * * *